US00PP09750P

United States Patent [19]

Carmi

[11] Patent Number: Plant 9,750

[45] Date of Patent: Dec. 17, 1996

[54] HYBRID TEA ROSE PLANT NAMED 'SEEMORE'

[75] Inventor: Carnel Carmi, Haydgev, Israel

[73] Assignee: Yoval Agricultural Products Ltd., Israel

[21] Appl. No.: 322,487

[22] Filed: Oct. 14, 1994

[51] Int. Cl.[6] ..... A01H 5/00

[52] U.S. Cl. ..... Plt./11

[58] Field of Search ..... Plt./11, 20, 21

[56] References Cited

U.S. PATENT DOCUMENTS

P.P. 4,391 3/1979 Delbard ..... Plt./20

P.P. 8,290 7/1993 Carmel ..... Plt./20

P.P. 8,620 3/1994 Carmel ..... Plt./20

*Primary Examiner*—Howard J. Locker

*Attorney, Agent, or Firm*—Pollock, Vande Sande & Priddy

[57] ABSTRACT

A new and distinct rose plant of the Hybrid Tea class named 'Seemore'. The plant is characterized by vigorous growth, non-fragrant flowers with purple red petals (R.H.S. 57 A-58 B on the inner side and R.H.S. 55D on the outer side), early and prolific flower production, and fast and good propagating features.

3 Drawing Sheets

CROSS REFERENCE TO RELATED PATENTS

The new and distinct cultivar described and illustrated herein is related to the cultivar 'Odem', which is the subject of U.S. Plant Pat. No. 8,620, issued Mar. 1, 1994.

FIELD OF THE INVENTION

The present invention is concerned with a new variety of a Hybrid Tea rose discovered by me and being a mutation of 'Odem', which is the subject of U.S. Plant Pat. No. 8,620 which is a mutation of 'Carola', which is the subject of U.S. Plant Pat. No. 8,290, issued Jul. 6, 1993, which in turn is a mutation of 'Deladel' ('Mme. G. Delbard'), which is the subject of U.S. Plant Pat. No. 4,391, issued Jul. 6, 1993.

BACKGROUND OF THE INVENTION

This mutation was discovered as a branch on an 'Odem' plant in 1993 on a cultivated area in a farm, located in Moshav Hayogev, located in Izra'el Valley, Israel, with an average night temperature of 25° C. in summer and 0°–5° C. in winter.

The branch was vegetatively propagated from cuttings by self-rooting. From these cuttings plants were grown in a green house where they were further vegetatively propagated from cuttings by self-rooting.

The resulting plants were found to be stable in their botanical characteristics, as are described below and as illustrated by typical plants parts in the attached photographs.

Asexual propagation of this new variety was performed at Moshav Ha-yogev, Israel.

The presently claimed cultivar was a natural mutation of the cultivar 'Odem'.

All color definitions in this application are taken from The Royal Horticultural Society of London, England, (R.H.S.) Colour Chart.

The data in the following table of comparison is based on observations made in the greenhouse at Moshav Ha'yogev, Israel, where plants were grown side-by-side, under the same conditions and under the same roof. The following observations were made between the present invention and a plant of the parent cultivar, 'Odem'.

| | 'ODEM' | 'SEEMORE' |
|---|---|---|
| Young shoot: | | |
| hue of anthocyanin coloration | purple | red-brown |
| Prickle(s): | | |
| shape: upper side | concave | concave to straight |
| Petiole: | | |
| rachis | smooth | hairy |
| Foliage: | | |
| color | RHS 145B yellow-green | RHS 141B light green |
| mature: color of lower side | red-green | green |
| Flowering stem: | | |
| length | 40–60 mm | 40–70 mm |
| Flower: | | |
| petals: average number | 40–43 | 43–58 |
| life on the plant | 12–18 days | 17–21 days |
| Petal: | | |
| color: upper side | RHS 46AB dark red Currant red | RHS 57A/58B purple red |
| lower side | RHS 52A deep red Crimson | RHS 55D whitish-purple very light purple |
| Stamen: | | |
| predominant color of filament | orange-red | yellow-orange |
| Stigma: | | |
| position as compared with anthers | same level | above |
| color | RHS 155C white | RHS 4D light yellow |
| Pollen | | |
| color | yellow-red | light yellow |
| Filament: | | |
| color | pink | yellow |

The relationship between the presently claimed cultivar to other related cultivars is as follows:

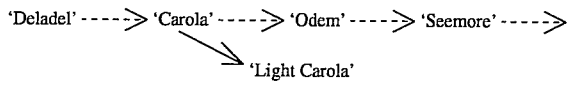

The following table of comparison present the differences between the cultivars in the family.

| U.S. Plant Pat./ Application | 'DELADEL' 4,391 | 'CAROLA' 8,290 | 'ODEM' 8,620 |
|---|---|---|---|
| Plant: | | | |
| growth habit | upright | upright | semi-upright |
| Stem: | | | |
| color: | green-brown corky | corky | green-brown |
| Young shoot: | | | |
| anthocyanin coloration | no data | strong | medium to strong |
| hue of anthocyanin | no data | red-brown | purple |
| Prickles: | | | |
| size: | | | |
| length (mm) | no data | 5 | 5 |
| height (mm) | no data | 6 | 6 |
| shape: upper side | long base hooked downward | concave to straight | concave |
| Short prickles: | | | |
| quantity per 10 cm at center of stem | many | 58 | none |
| Long prickles: | | | |
| quantity per 10 cm at center of stem | many | 8 | 7 |
| Leaf: | | | |
| size: | | | |
| length (mm) | no data | 140–170 | 120–150 |
| width (mm) | no data | 110–150 | 75–115 |
| green color | no data | medium to dark | medium |
| glossiness of upper side | no data | absent to very weak | weak |
| Leaflet: | | | |
| cross section | oval pointed, often curved with convex upper surface | slightly convex | straight |
| undulation of margin | no data | absent to very weak | weak to medium |
| Terminal leaflet: | | | |
| width: (mm) | no data | ca. 35 | 30–43 |
| blade: length (mm) | no data | ca. 60 | 50–65 |
| Petiole: | | | |
| length (mm) | no data | ca. 20 | 15–20 |
| rachis | color, green | hairy | smooth |
| Foliage: | | | |
| young: color of upper side | light brown | RHS 144B yellow-green | RHS 145B yellow-green |

-continued

| | | | |
|---|---|---|---|
| mature: color of lower side | green | red-green | red-green |
| Flowering stem: | | | |
| length (cm) | 70–90 | 70–80 | 40–60 |
| color | no data | medium green | green |
| Flower pedicel: | | | |
| number of hairs or prickles | no data | few | very few to few |
| Flower bud: | | | |
| longitudinal section | pointed ovoid | circular | ovoid |
| Flower: | | | |
| diameter (mm) | average 102–114 | ca. 110 | ca. 80 |
| bloom height (mm) | no data | large 50–70 | medium 30–50 |
| fading with age | none to end of third day | none | slight fading begins after 7–10 days |
| view from above | rounded | rounded to star shaped | rounded |
| fragrance | slight not sweet nor spicy | none | none |
| number of petals | 30–35 | 33–40 | 40–43 |
| life (days): | | | |
| on the plant | no data | 20–30 | 15–20 |
| in a vase | no data | 12–15 | 15–18 |
| Sepal: | | | |
| length (mm) | no data | 40–55 | 30–43 |
| extensions | slight | strong | medium |
| Petal: | | | |
| size: | | | |
| length (mm) | no data | 50–60 | 37–45 |
| width (mm) | no data | 55–65 | 39–59 |
| upper side: color | Blood red | RHS 53A dark red | RHS 46AB dark red Currant red |
| basal spot at base of petal: size | very small small | medium | small |
| color | yellow | RHS 155D white | RHS 3B yellow |
| lower side: color | Blood red | RHS 53C dark red | RHS 52A deep red Crimson |
| reflexing of margin | strong | strong | medium |
| undulation of margin | no data | weak | very weak to weak |
| Stamen: | | | |
| predominant color of filament | yellow | purple | orange-red |
| Style: | | | |
| hairiness of upper half | no data | medium | absent |
| Stigma: | | | |
| position as compared with anthers | no data | above | same level |
| color | Amber yellow | RHS 4C light yellow | RHS 155C white |
| Seed vessel: | | | |
| size: | no data | medium | small |
| length (mm) | no data | 11 | 8 |
| diameter (mm) | no data | 12 | 11 |
| shape of | no data | pitcher | funnel |

-continued

| | | | |
|---|---|---|---|
| longitudinal section | | shaped | shaped |
| Pollen: | | | |
| color | Gold yellow | red-yellow | yellow-red |
| Anthers: | | | |
| color | yellow | red | yellow |
| Filament: | | | |
| color | yellow-red | yellow-red | pink margin: orange |

| U.S. Plant Pat./ Application | 'LIGHT CAROLA' 08/323,076 | 'SEEMORE' 08/322,487 |
|---|---|---|
| Plant: | | |
| growth habit | upright | semi-upright |
| Stem: | | |
| color: mature | green-brown, corky | green-brown |
| Young shoot: | | |
| anthocyanin coloration | strong | medium to strong |
| hue of anthocyanin | red-brown | red-brown |
| Prickles: | | |
| size: | | |
| length (mm) | 4.5 | 5 |
| height (mm) | 5.5 | 6 |
| shape: upper side | straight | concave to straight |
| Short prickles: | | |
| quantity per 10 cm at center of stem | 59 | none |
| Long prickles: | | |
| quantity per 10 cm at center of stem | 9 | 8 |
| Leaf: | | |
| size: | | |
| length (mm) | 140–160 | 120–150 |
| width (mm) | 100–130 | 75–115 |
| green color | medium to dark | medium |
| glossiness of upper side | absent to very weak | weak |
| Leaflet: | | |
| cross section | slightly convex | straight |
| undulation of margin | absent to very weak | weak to medium |
| Terminal leaflet: | | |
| width: (mm) | ca. 33–38 | 30–43 |
| blade: length (mm) | ca. 60 | 50–65 |
| Petiole: | | |
| length (mm) | ca. 20–25 | 15–20 |
| rachis | smooth | hairy |
| Foliage: | | |
| young: color of upper side | RHS 141B light green | RHS 141B light green |
| mature: color of lower side | green | green |
| Flowering stem: | | |
| length (cm) | 60–80 | 40–70 |
| color | green | light green |
| Flower pedicel: | | |
| number of hairs or prickles | few | very few to few |
| Flower bud: | | |
| longitudinal section | circular | ovoid |
| Flower: | | |
| diameter (mm) | ca. 100 | ca. 80 |
| bloom height (mm) | large 50–70 | medium 30–50 |
| fading with age | none | fading begins after 7–10 days |
| view from above | rounded to star shaped | rounded |
| fragrance | none | none |
| number of petals | 28–39 | 43–58 |
| life (days): | | |
| on the plant | 20–30 | 17–21 |
| in a vase | 12–15 | 12–15 |
| Sepal: | | |
| length (mm) | 35–48 | 30–43 |
| extensions | strong | medium |
| Petal: | | |
| size: | | |
| length (mm) | 40–60 | 37–45 |
| width (mm) | 40–50 | 39–49 |
| upper side: color | RHS 47A/57B red | RHS 57A/58B purple red |
| basal spot at base of petal: size | medium | small |
| color | RHS 155A white | RHS 3B yellow |
| lower side: color | RHS 52A red | RHS 55D whitish-purple, very light purple |
| reflexing of margin | strong | medium |
| undulation of margin | weak | very weak to weak |
| Stamen: | | |
| predominant color of filament | purple | yellow-orange |
| Style: | | |
| hairiness of upper half | medium | absent |
| Stigma: | | |
| position as compared with anthers | above | above |
| color | RHS 4C light yellow | RHS 4D light yellow |
| Seed vessel: | | |
| size: | medium | small |
| length (mm) | 11 | 8 |
| diameter (mm) | 12 | 7 |
| shape of longitudinal section | pitcher shaped | funnel shaped |

-continued

| | | |
|---|---|---|
| Pollen: | | |
| color | red-yellow | light yellow |
| Anthers: | | |
| color | red | light yellow |
| Filament: | | |
| color | yellow-red | yellow |

SUMMARY OF THE INVENTION

The present invention provides a Hybrid Tea rose variety which includes the following characteristics which distinguish the new variety from the cultivar 'Odem', to which it is related, and for which the following differences have been noted:

Young shoot: Hue of anthocyanin coloration.
Prickles: Shape upper.
Petiole: Rachis.
Foliage: Color.
Flower stem: Length.
Flower: Number of petals, life on the plant.
Petal: Color.
Stamen: Predominant color of filament.
Stigma: Position as compared with anthers, color.
Pollen: Color.
Filament: Color.

BRIEF DESCRIPTION OF THE DRAWINGS

Sheet 1 represents a typical specimen of the present invention, illustrating a flower bud at picking stage, a part of the stem, leaflets, and flowers at various opening stages;

Sheet 2 represents a side-by-side comparison of the flower size, bud size and color of petal between a typical specimen of the present invention, 'Seemore' (on the left) and the parent variety, 'Odem' (on the right); and Sheet 3 represents another side-by-side comparison of various flower parts between a typical specimen of the present invention, 'Seemore' (on the left) and the parent variety, 'Odem' (on the right).

The colors in the drawings are as true as is reasonably possible in an illustration, depicting green and red colors. The plants illustrated in Sheets 2 and 3 were grown under exactly the same conditions, in a greenhouse, at Moshav Ha'yogev, each on its own roots, and being visibly healthy.

BOTANICAL DESCRIPTION

The following observations were made in Moshav Ha'yogev, Israel in 1993 in a greenhouse:

Plant:
- *Form.*—Bush.
- *Growth habit.*—Semi-upright.
- *Height (cm).*—150–200.
- *Spread (cm).*—Ca. 80.

Wood:
- *Color.*—Mature: Light brown.
- *Bark.*—Color: young: green. mature: light brown.

Stem:
- *Color.*—Young: R.H.S. 146 B yellow green. Mature: R.H.S. 143 A green.

Young shoot:
- *Anthocyanin coloration.*—Medium to strong.
- *Hue of anthocyanin coloration.*—Red-brown.

Prickle(s): present.
- *Size.*—Length (mm): ca. 5. Height (mm): ca. 6.
- *Shape.*—Upper side: concave to straight. Lower side: concave.
- *Color.*—Young: R.H.S. 176 A grey orange. Mature: R.H.S. 173 A grey orange.

Short prickles:
- *Quantity.*—Few.

Long prickles:
- *Quantity per 10 cm at center of stem.*—Few (8).

Leaf:
- *Size.*—Length (mm): 120–150. Width (mm): 75–115.
- *Green color.*—Medium.
- *Glossiness of upper side.*—Weak.
- *Number of leaflets in the compound leaf.*—3, 5, or 7.

Leaflet:
- *Cross section.*—Straight.
- *Undulation of margin.*—Weak to medium.
- *Margin.*—Serrated.

Terminal leaflet:
- *Length of blade (mm).*—50–65.
- *Maximum width (mm).*—30–43.
- *Shape of base.*—Rounded.

Petiole:
- *Length (mm).*—15–20.
- *Rachis.*—Straight, flat, hairy.
- *Color.*—R.H.S. 143 A/144 A green.

Foliage:
- *Young.*—Color: upper side: center: R.H.S. 152 A yellow green. rims: R.H.S. 166 AB grey orange. lower side: R.H.S. 176 AB grey orange.
- *Mature.*—Color upper side: R.H.S. 137 A green. lower side: R.H.S. 137 C/138 A green.

Stipule: Stitched, split tip.

Bloom:
- *Borne.*—Multiply/in a cluster.

Flowering shoot:
- *Number of flowers.*—Few (3–5).

Flowering habit: Continuous.

Flowering stem:
- *Length (cm).*—40–70.
- *Color.*—Light green.

Flowering pedicel:
- *Number of hairs or prickles.*—Very few to few.

Flower bud:
- *Longitudinal section.*—Ovoid.
- *Size.*—Medium (30–50 mm).

Flower:
- *Type.*—Double.
- *Diameter (mm).*—Ca. 80.
- *Fragrance.*—None.
- *View from above.*—Rounded.
- *Side view.*—Upper side: flattened-convex. Lower side: flat.
- *Number of petals.*—43–58.
- *Life.*—On the plant 17–21 days. In a vase: 12–15 days.
- *Fading with age.*—Begins after 7–10 days.

Sepal:
- *Length (mm).*—30–43.
- *Extensions.*—Medium.
- *Color.*—Upper side: R.H.S. 143 B/144 C green-yellow green. Lower side: R.H.S. 144 A yellow green.

Petal:
- *Size.*—Length (mm): 37–45. Width (mm): 39–49.
- *Shape.*—*Rounded.*

*Upper side.*—Color: middle zone: R.H.S. 57A/588 purple red. marginal zone: R.H.S. 57A/58B purple red. Basal spot: present. Basal spot: size: small. color: R.H.S. 3B yellow.

*Lower side.*—Color: middle zone: R.H.S. 55D whitish-purple. marginal zone: R.H.S. 55D whitish-purple. Basal spot: present. Basal spot: color: R.H.S. 3D light yellow.

*Reflexing of margin.*—Medium.

*Undulation of margin.*—Very weak to weak.

Stamen:

*Predominant color of filament.*—Yellow-orange.

Style:

*Length.*—Long.

*Predominant color.*—Purple.

*Hairiness of upper half.*—Absent.

Stigma:

*Position as compared with anthers.*—Above.

*Color.*—R.H.S. 4D light yellow.

Seed vessel:

*Size.*—Small.

*Length (mm).*—Ca. 8.

*Diameter (mm).*—Ca. 7.

*Shape of longitudinal section.*—Funnel shaped.

*Color.*—Green.

*Description.*—Long, hairy.

Pollen: Light yellow.

Anthers:

*Color.*—Light yellow.

*Quantity.*—Many.

*Arrangement.*—Peripheral.

Filament:

*Color.*—Yellow.

*Description.*—Folded, flat.

Time from planting to beginning of flowering: 3–4 months.

Self-rooting: Very good.

The cultivar is intended as and is suitable as a greenhouse rose. The cultivar bears blooms multiply. Blooms may be borne in a cluster.

When reference is made herein to "Number of flowers few," it is understood that such refers to 3, 5, or 7 flowers per cluster (i.e., the flowers that are left on the flowering shoot after the other flowers were pruned off). In addition, the term "fast" represents: within one month from insertion (of the cutting into the bedding) to a commercial plant. The term "good" represents about 60–70% success in propagation.

I claim:

1. A new and distinct rose plant of the Hybrid Tea class named 'Seemore' as shown and described; said plant being characterized by vigorous growth, non-fragrant flowers with purple red petals (R.H.S. 57 A-58 B on the inner side and R.H.S. 55D on the outer side), early and prolific flower production, and fast and good propagating features.

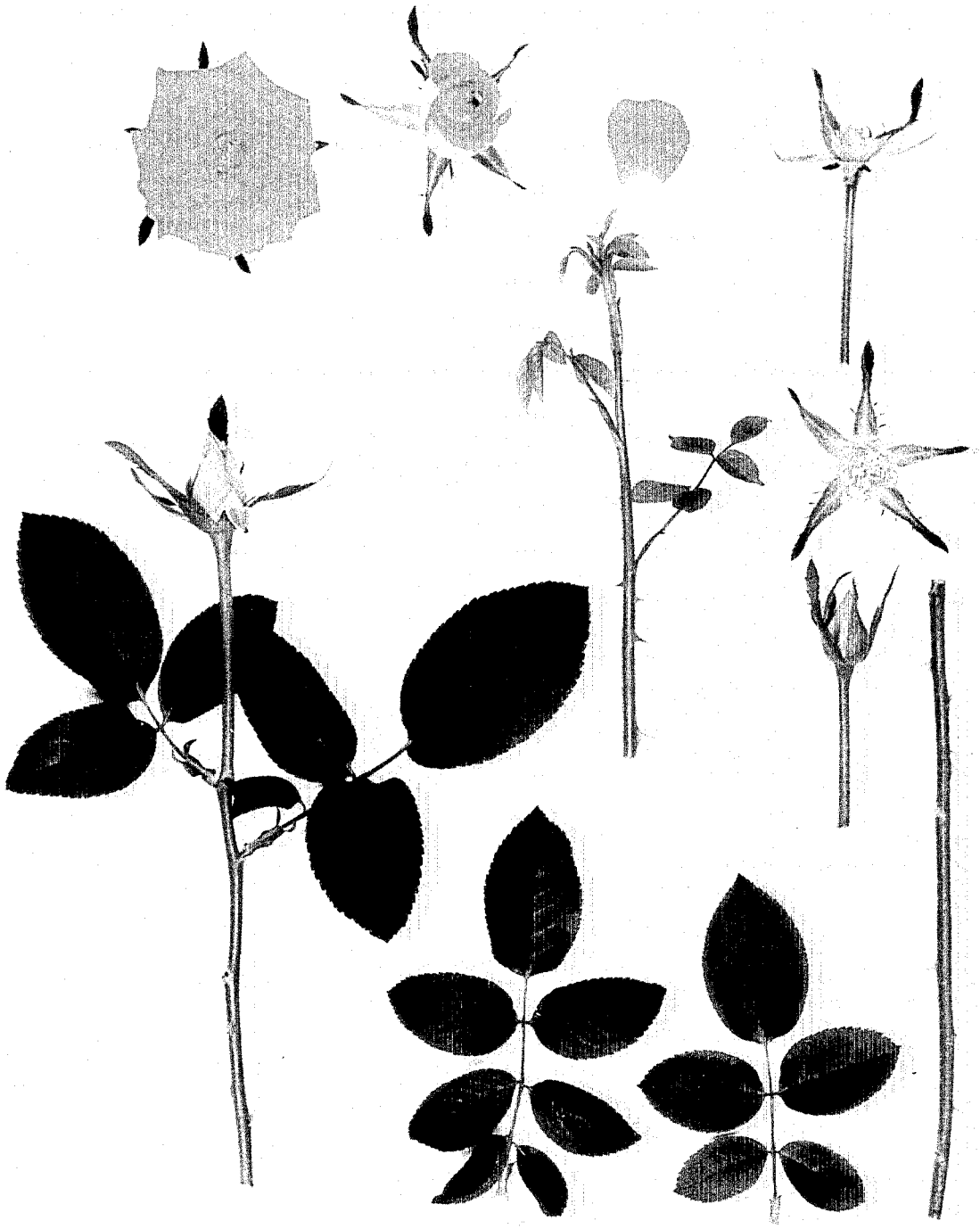

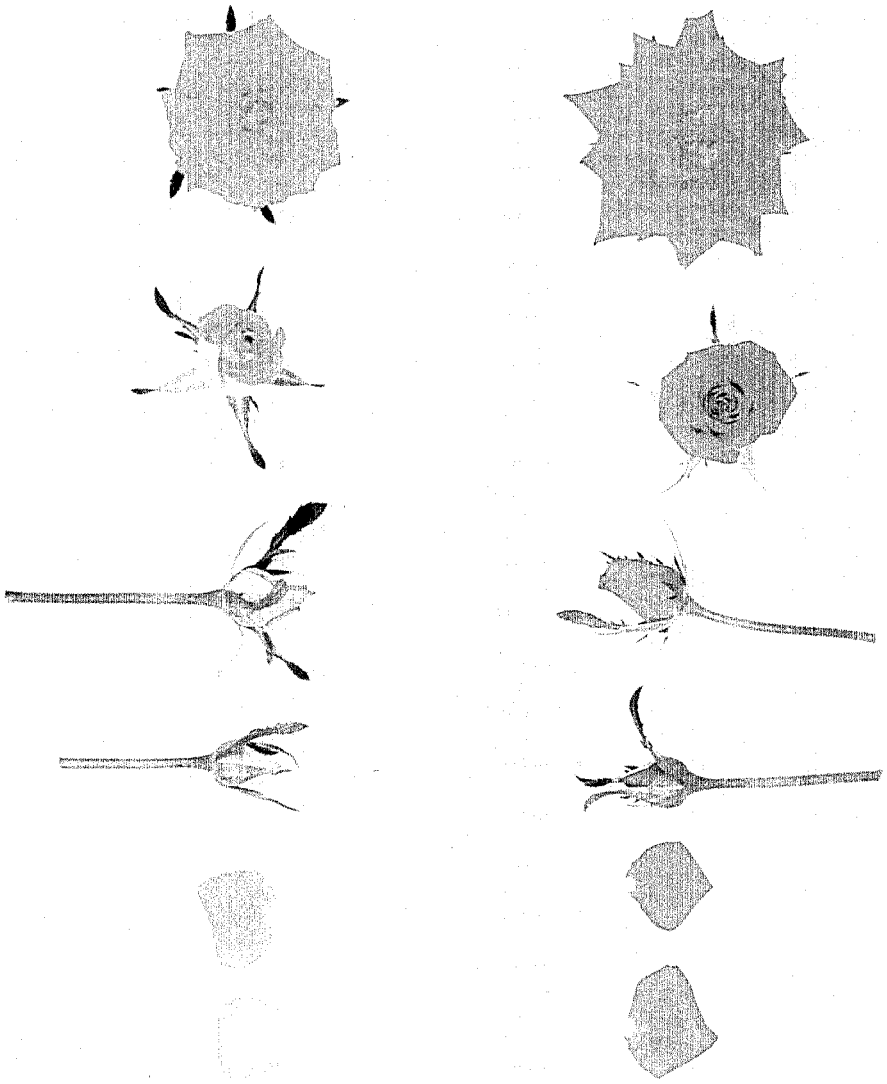

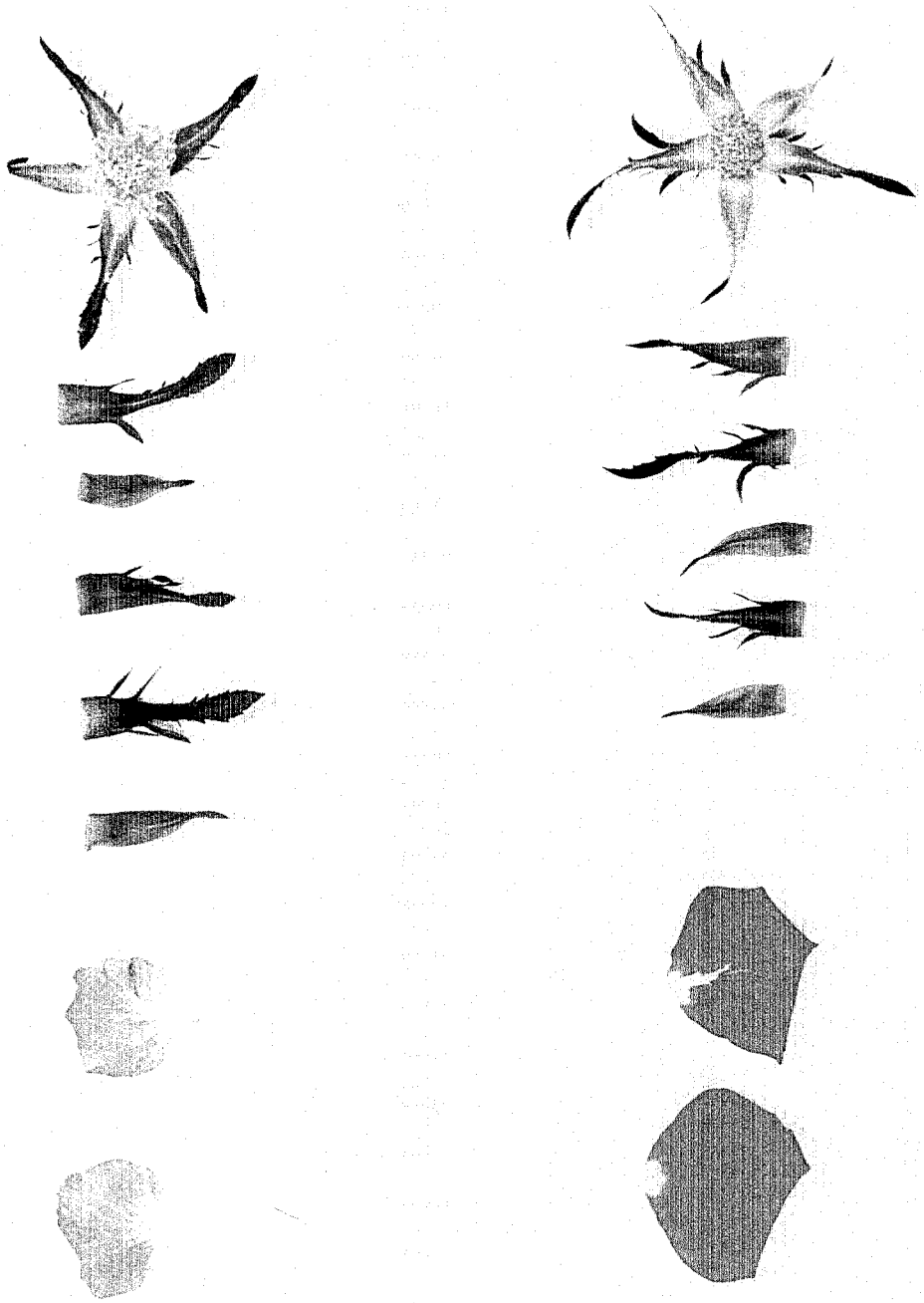

* * * * *